United States Patent [19]
Specht

[11] 4,264,988
[45] May 5, 1981

[54] PROTECTIVE SPLASH GOGGLE
[75] Inventor: Paul B. Specht, Wilmette, Ill.
[73] Assignee: Vallen Corporation, Houston, Tex.
[21] Appl. No.: 848,514
[22] Filed: Nov. 4, 1977
[51] Int. Cl.² ............................................. A61F 9/02
[52] U.S. Cl. ...................................................... 2/431
[58] Field of Search .................. 2/436, 426, 437, 431, 2/439, 445, 446, 428, 435, 10, 441

[56] References Cited
U.S. PATENT DOCUMENTS

| | | | |
|---|---|---|---|
| 2,877,463 | 3/1959 | Watkins | 2/437 |
| 2,903,700 | 9/1959 | Finken et al. | 2/10 |
| 3,000,011 | 9/1961 | Sterne et al. | 2/436 |
| 3,081,461 | 3/1963 | Gurtowski | 2/441 |
| 3,141,172 | 7/1964 | Hirschmann | 2/436 |
| 3,368,221 | 2/1968 | Anderson | 2/437 |
| 3,418,658 | 12/1968 | Danico | 2/436 |
| 3,638,240 | 2/1972 | Militello | 2/437 |
| 4,070,712 | 1/1978 | Marwitz | 2/10 |

*Primary Examiner*—Werner H. Schroeder
*Assistant Examiner*—A. M. Falik
*Attorney, Agent, or Firm*—Pravel, Gambrell, Hewitt, Kirk, Kimball & Dodge

[57] ABSTRACT

A protective goggle for protecting a wearer's face from the entry of chemical splash or other deleterious liquids into the protected facial region including a goggle frame and lens adapted for mounting on the wearer, the goggle frame having an opening for allowing for air transfer into and out of the goggle frame; a shield cap mounted onto the goggle frame over the frame opening for providing a shield opening which is in fluid communication with the frame opening; and, a recessed channel formed with the goggle frame between the shield opening and the goggle frame opening for directing any deleterious fluids entering the shield opening away from the frame opening thereby preventing the entry of such deleterious fluids into the facial region protected by the goggles.

8 Claims, 5 Drawing Figures

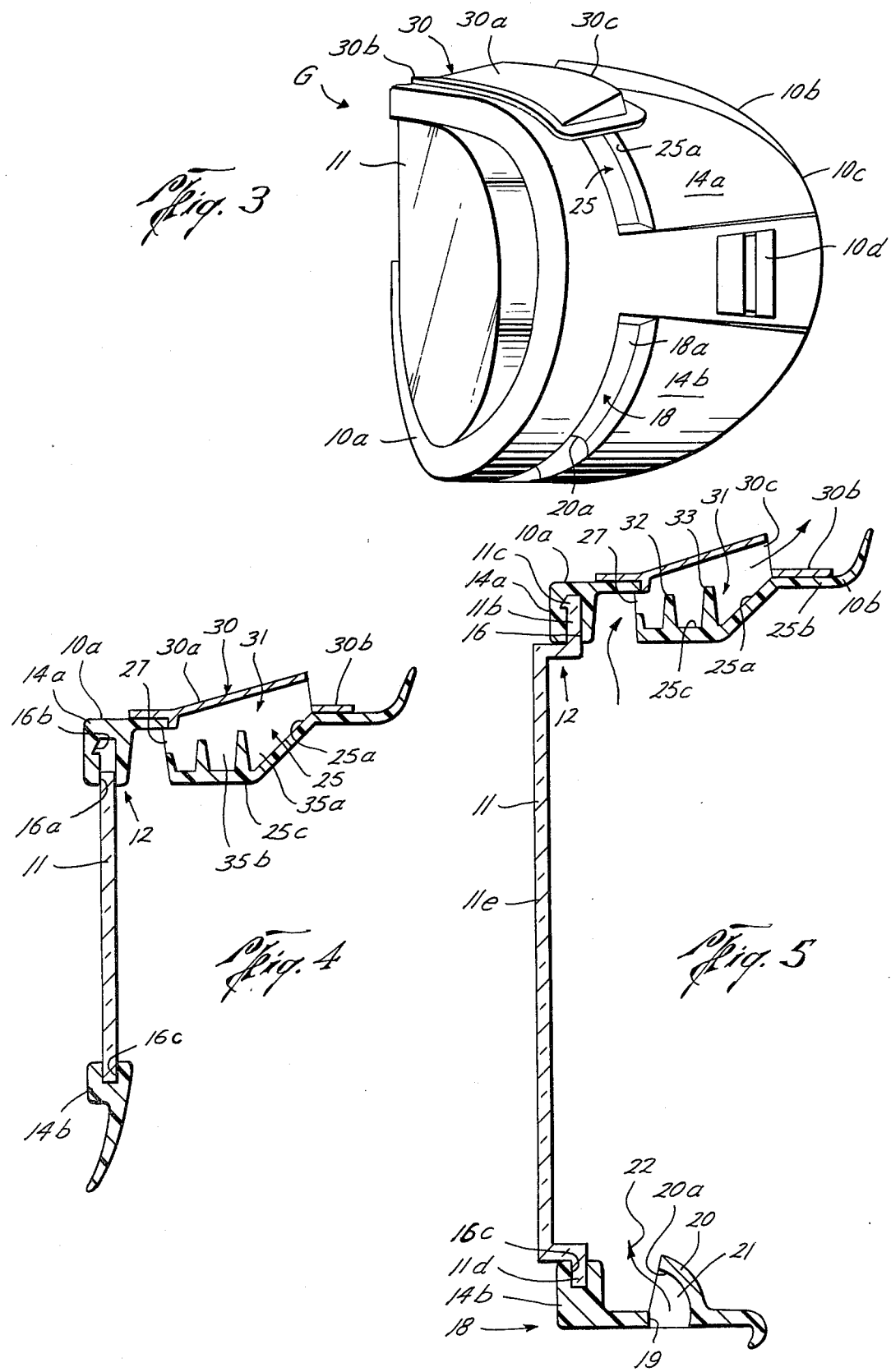

PROTECTIVE SPLASH GOGGLE

BACKGROUND OF THE INVENTION

The field of this invention is protective goggles for protecting the wearer from chemical splash and other deleterious materials.

The purpose of goggles is to protect the eye region of the wearer from outside elements. For example, in the field of sports, such outside elements may be snow for the skier or simply dust for the motorcyclist. Goggles are also heavily used in industry where the purpose of the goggles is to protect against the splash of chemical or other deleterious liquids.

For the purposes of describing prior art, goggles may be classified into three groups: goggles without ventilation; goggles with openings for ventilation; and, goggles with shielded openings to at least in part prevent the entry of deleterious materials such as chemical splash into the protected eye region of the wearer. The protective goggle of this invention is particularly directed to the latter category of goggles.

There are a substantial number of patents which disclose goggles of various types and styles, but having no ventilation openings. A list of such goggles in chronological order are as follows: U.S. Pat. Nos. Des. 138,545; Des. 140,312; 2,589,575; Des. 171,762; 2,688,135; 2,706,815; Des 175,015; Des. 177,581; 2,770,807; Des. 182,463; Des. 186,792; Des. 207,127; Des. 207,796; Des. 214,258; 3,484,156; 3,505,680; and, Des. 232,983. This list of patents directed to goggles without ventilation means is not exhaustive.

The second group of patents relates to goggles having exposed ventilation openings in various configurations and sizes: U.S. Pat. Nos. Des. 136,379; 2,368,750; Des. 140,805; Des. 142,221; 2,406,998; 2,422,534; 2,573,722; Des. 166,231; Des. 166,257; 2,598,265; 2,603,785; 2,608,687; 2,617,100; Des. 168,936; Des. 168,988; 2,645,775; 2,680,846; 2,680,882; Des. 176,309; 2,773,260; Des. 180,892; Des. 181,456; 2,877,462; 2,903,700; 2,914,770; 2,936,459; 2,979,728; 3,012,248; Des. 204,099; 3,274,614; 3,298,031; 3,368,221; 3,395,406; 3,517,393; 3,591,864; Des. 223,983; 3,718,937; 3,896,496; 3,931,646; and, Des. 242,666. This list of patents in this second category is not exhaustive.

The third category, goggles with shields, include U.S. Pat. No. 3,638,240 of Militello. The Militello patent '240 discloses vented goggles wherein the vent structure is made of a molded plastic and includes an oblong opening in the goggle plastic frame having a surrounding wall extending outwardly from the frame together with an oblong plastic cap which mounts over the wall in sealing engagement therewith. The plastic cap has an opening along the lower part of its rear wall whereby air may pass through the cap opening and over the outwardly extending wall of the frame and enter through the frame opening. The rear opening disclosed in the Militello patent prevents at least to some extent splatter or spray material entering the space behind the lens while still allowing air circulation.

U.S. Pat. No. 3,000,011 of Sterne et al. discloses sets of openings in a safety goggle frame wherein each opening is surrounded by an outwardly directed flange to provide a dam or barrier against flow of moisture into the goggle frame openings. The flange-surrounded openings are covered with a cap or shield to prevent direct entry of undesirable materials into the opening. Therefore, the Sterne patent '011 and the Militello patent '240 disclose very similar concepts.

U.S. Pat. No. 2,877,463 of Watkins discloses a goggle frame having an oblong opening which extends across the entire top of the frame and is covered by an oblong panel having alternately spaced flanges for allowing only indirect entry of air or other fluid into the area of the oblong opening.

U.S. Pat. No. 3,141,172 of Hirschmann discloses a ventilated goggle which includes a tubular base which extends outwardly through an opening in the frame member and has a ventilated cap mounted thereover. The openings for the ventilated cap are indirectly in fluid communication with the actual opening in the tubular base in order to prevent direct fluid transfer from the openings in the ventilating cap through the frame opening. According to the disclosure in the Hirschmann patent, it is contemplated that one of the openings in the ventilating cap may, in addition to providing ventilation, open downwardly for the drainout of liquid which may accidentally enter the cap.

U.S. Pat. No. 3,418,658 of Danico discloses a similar type of circular ventilating cap which is designed to prevent the direct entry of foreign matter through the cap openings into the goggle frame opening over which the cap is mounted. U.S. Pat. Nos. 3,081,461; 2,715,223; and, 2,395,297 also disclose ventilation systems that perhaps belong in this third category in that goggle frame openings are at least partly shielded.

SUMMARY OF THE INVENTION

This invention relates to a new protective goggle design for preventing the transfer of undesirable substances such as chemical splash into the interior goggle area while at the same time allowing for air flow through the goggles in order to prevent moisture accumulation and fogging of the lens and the like. The protective goggle of the preferred embodiment of this invention includes a goggle frame having a front portion which includes means for mounting a lens and a rear portion having a periphery contoured to engage the face of the wearer. The goggle frame may be further divided into a top portion and a bottom portion for the purposes of description. The goggle frame has an opening therein to allow for the transfer of air into or out of the goggle frame. Shield means are mounted onto the frame over the frame opening for providing a shield opening which is in fluid communication with the frame opening. The goggle frame further includes a fluid drain means positioned between the goggle frame opening and the shield opening for preventing fluid flow transfer through the goggle frame opening by transferring fluid entering the shield opening away from said goggle opening to thereby substantially prevent the undesirable entry of chemical splash or other deleterious materials into the goggle frame and thus into contact with the eyes of the wearer. This summary of the invention is not intended to be exhaustive of all the potentially patentable and valuable features of this invention, but is merely intended to summarize some of those features.

BRIEF DESCRIPTION OF THE DRAWINGS

FIG. 3 is a side view of the protective goggle;

FIG. 4 is a sectional view taken along line 4—4 of FIG. 1 to illustrate sectionally the structure of the protective goggle at its vertical midline; and FIG. 5 is a sectional view taken along line 5—5 of FIG. 1 illustrating the shield and fluid drain structure formed in the top portion of the goggle frame and forming an important part of this invention.

DESCRIPTION OF THE PREFERRED EMBODIMENT

The protective goggle G of the preferred embodiment of this invention may find use in industry or in other areas such as sports such as skiing. Industrial use of the protective goggle G of this invention includes uses in machine shops in grinding, sanding activities, uses in the field in chipping and the like; and, uses in chemical plants and other areas where workers may be subject to splashing chemicals or other deleterious materials. The goggle G may also be used for general purpose eye protection needed during mowing and other general activities. Basically, the protective goggle G of this invention may be used in any activity wherein it is desirable to prevent the entry of foreign materials into the region protected by the goggle while allowing for air flow into and out of the protected region. For the purpose of simplicity in explanation, the advantages and use of the protective goggle G of the preferred embodiment of this invention will be described with respect to the prevention of the entry of chemical splash into the region protected by the goggle.

Figure 1:
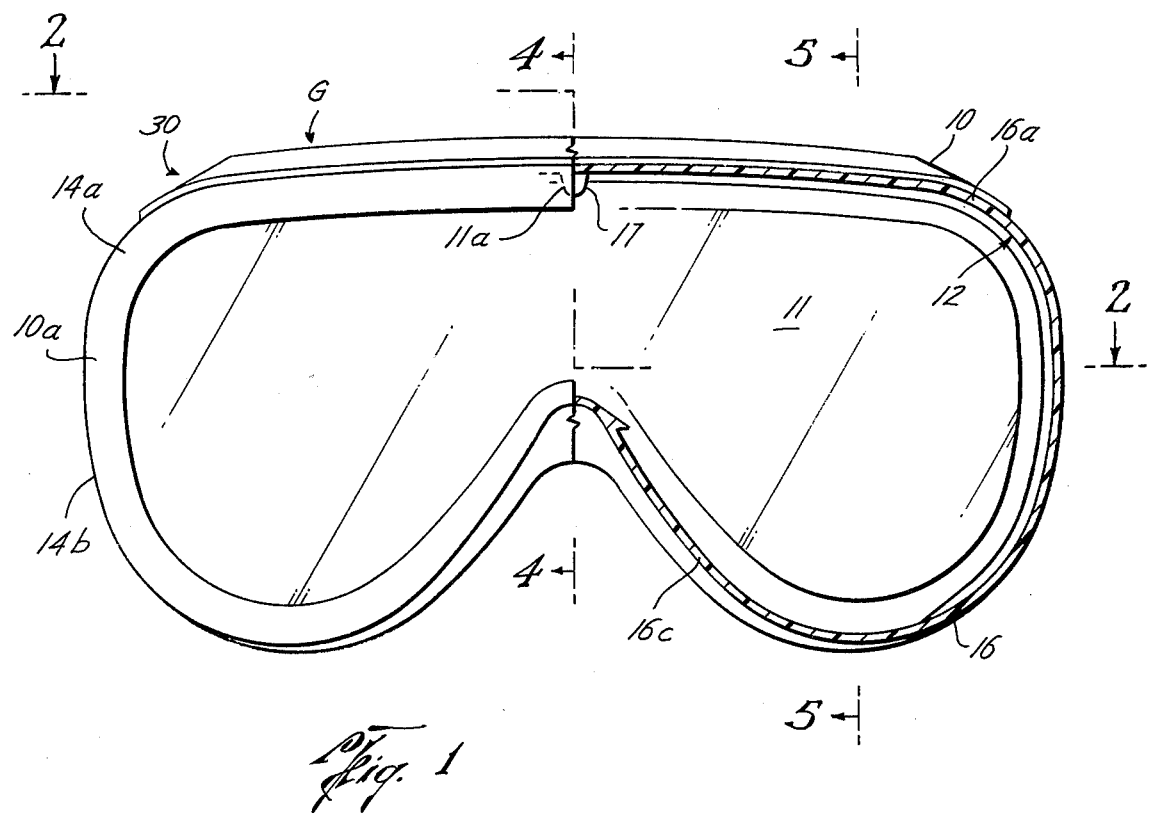
FIG. 1 is a front view of the protective goggle of the preferred embodiment of this invention with a sectional view of one-half of the goggle to illustrate in particular the mounting of the lens.

The protective goggle G of the preferred embodiment of this invention includes a frame generally designated as 10 which mounts a lens generally designated as 11. The goggle frame 10 may be made of material such as rubber or plastic and will generally be molded as are most goggle frames presently manufactured. The goggle frame 10 includes a front portion 10a which includes means generally designated by the number 12 for mounting the lens 11. The front portion 10a of the goggle frame 10 is basically convex in configuration and is shown clearly in FIGS. 2 and 3. The goggle frame 10 may further be defined as having a rear portion 10b which is integrally formed with the front frame portion 10a. The rear frame portion 10b terminates in a rear periphery or contour edge 10c designed to fit against the facial area of the wearer which surrounds the wearer's eyes. The basic peripheral configuration of the rear portion 10b of the goggle frame 10 is well known in the art and will not be discussed further. The goggle frame 10 further includes strap connecting portions 10d which may be integrally formed with the goggle frame for mounting a strap end of a strap (not shown) for positioning about the head of the wearer to hold the goggle G in place as is well known in the goggle art. For the purposes of discussion, the goggle frame 10 may further be divided into a top half 14a above the righthand portion of section line 2—2 in FIG. 1. A bottom half 14b of the goggle frame is defined as the portion of the goggles below the righthand part of section line 2—2 in FIG. 1, it being assumed that the righthand portion of the section line 2—2 of FIG. 1 is approximately located at the same level as the eyes of the wearer. Thus, for definition purposes, the top half 14a of the frame is located above a middle line through the wearer's eyes; and, the bottom half 14b is below such line. This definition is just for description purposes and is not to be construed as a limitation on this invention.

The lens mounting means 12 is formed by a continuous groove 16 formed in the interior of the front goggle portion 10a. The groove 16 follows the curvature of the front portion of the goggle and is thus basically convex as viewed from the top and has two lower curved portions which are connected by an inverted V-shape portion fitting over the bridge of the nose. This configuration is of course known in the goggle art as generally following the configuration of the eyes and nose. The groove 16 includes an upper groove portion 16a having an enlarged end 16b while lower groove portion 16c is simply a rectangular recess. A detent portion 17 of the front goggle actually extends into the top groove portion 16a and is alignable with a corresponding notch 11a in the lens 11. Utilization of the frame detent 17 in cooperation with the lens notch 11a provides for instant positioning and thus alignment of the lens 11 in the goggle frame 10. The upper edge 11b of the lens 11 includes an enlarged end section 11c adapted to fit into the enlarged groove portion 16b for holding the lens 11 in place. The bottom and side edges 11d of the lens 11 may be rectangular to fit in the frame rectangular groove shown as 16c in FIGS. 4 and 5. The lens 11 thus includes an edge configuration formed by top edge 11c and bottom edge 11d. A central part 11e of the lens is raised. The lens 11 is also convex as viewed from the top.

Figure 2:
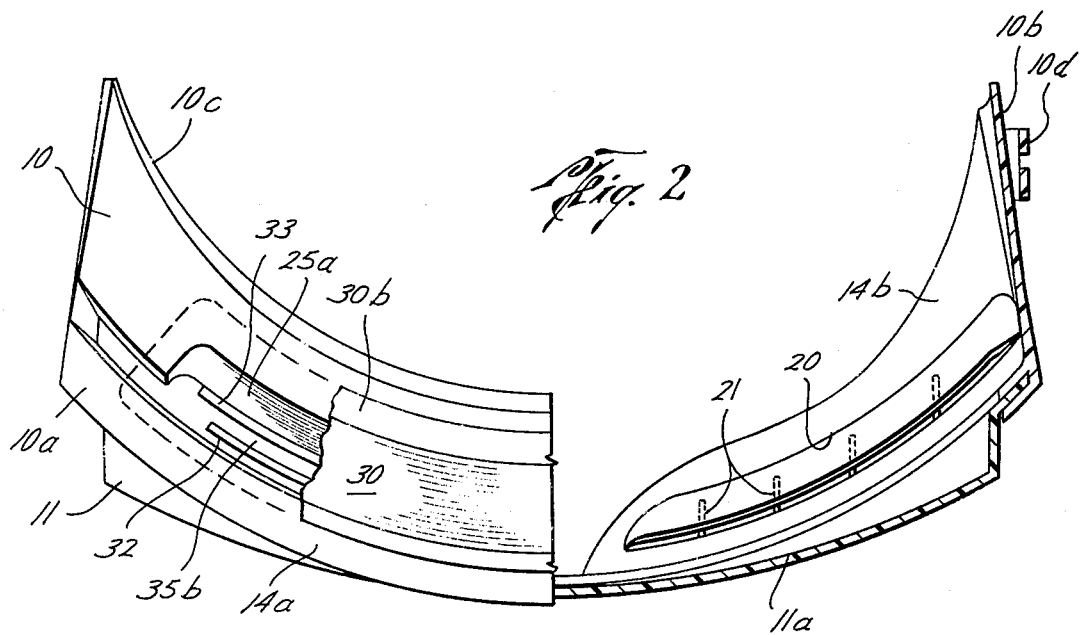
FIG. 2 is a sectional view taken along stepped line 2—2 of FIG. 1 illustrating the top and the bottom of the goggle frame.

The lower goggle frame portion 14b includes a groove arrangement generally designated by the number 18 which is positioned in the bottom of the righthand goggle frame section. A similar groove arrangement 18 (not shown) is positioned in the lefthand section of the bottom frame portion 14b. Referring in particular to FIGS. 2, 3 and 5, the groove arrangement generally designated as 18 includes groove 18a which extends downwardly from about the middle of the goggle frame to an opening 19. The lower portion of the goggle frame includes a curved entry section 20 which is supported by spaced ribs 21 to allow the entry of air as shown by arrow 22 into the protected region of the wearer. The curved entry section or shield 20 extends over the opening 19 such that chemical splash directed vertically upwardly will actually hit against interior curved surface 20a and drain back out of the bottom opening 19. In this manner, air is allowed to flow into or out of the interior region protected by the goggle G but the introduction of undesirable elements such as chemical splash is prevented by the curved section 20.

The top portion 14a of the goggle frame includes a groove or channel generally designated by the number 25 which extends from about the mid-section of each side of the goggle frame all the way across the top portion 14a. The groove 25 includes an inclined ramp portion 25a which extends at an incline downwardly from a flat section 25b of the rear portion 10b of the goggle frame 10. The inclined portion 25a terminates in a recessed horizontal portion 25c integrally formed therewith which forms the bottom of the groove 25a. The third face of the groove 25 includes a solid, front portion which is not actually illustrated in the drawings because of the location of an oblong frame opening 27 in a substantial part of the groove 25. The frame opening 27 is thus in an approximate vertical plane, almost being at a right angle with respect to the groove bottom 25c.

The opening 27 is completely covered by a shield means generally designated by the number 30.

The shield means 30 includes a central raised portion or body 30a which is surrounded by an edge portion 30b, the edge portion 30b being mounted onto the top portion 14a of the frame body at the front and rear of the groove 25 over that portion of the groove wherein the opening 27 is located. The central shield portion 30a is inclined upwardly from the front towards the rear of the goggle frame 10 but has an opening 30c therein which faces rearwardly of the goggle frame 10. The shield opening 30c is therefore in fluid communication with the frame opening 27 that is separated or spaced therefrom by the combination of the groove ramp section 25a and the groove horizontal section or bottom 25c.

The groove 25 includes a fluid drain means formed within the groove 25 and generally designated by the number 31 positioned between the goggle frame opening 27 and shield frame opening 30b for preventing the transfer of chemical splash into the frame opening 27 by transferring any fluid such as chemical splash which enters the shield opening 30c away from the goggle frame opening 27. The fluid drain means 31 is actually formed by the groove 25 in cooperation with parallel ridges 32 and 33 which extend upwardly and are integrally formed with the bottom groove section 25c to form drain passages 35a and 35b which are in fluid communication with the portion of the groove 25 not covered by the shield means 30. The parallel ridges 32 and 33 are aligned with opening 27 to protect the opening against the entry of foreign materials.

In operation and use, chemical splash directed from the front of the goggles is not likely to enter the shield opening 30c because the shield opening 30b faces rearwardly. But in the event such chemical splash does enter the opening 30b, the ridges 32 and 33 integrally formed with the bottom groove section 25c and inclined groove section 25a cooperate to cause the draining of the intruding chemical splash downwardly out from under the shield means 30 and into the exposed groove portion of groove 25 and thus outwardly of the goggle frame. In this manner, chemical splash or other deleterious fluids are prevented from entering the frame opening 27 by the combination of the ridges 32 and 33 within the recessed groove 25, which cooperates with the shield means 30 to prevent the entry of deleterious fluids into the goggled area or region of the wearer. At the same time, the combination of the lower openings 19 and the ventilating arrangement including shield means 30 and protected opening 27 allow for the circulation of air through the interior of the goggles, thus preventing any buildup of moisture and the like.

The foregoing disclosure and description of the invention are illustrative and explanatory thereof, and various changes in the size, shape and materials as well as in the details of the illustrated construction may be made without departing from the spirit of the invention. For example, the goggle G may be used with or without spectacles. An additional advantage of the goggle G is the use of a curved lens that eliminates tunnel vision found in many soft body safety and chemical goggles.

I claim:

1. A protective goggle for protecting the eye area of a wearer's face from the entry of chemical splash or other foreign substances, comprising:
    a goggle frame and lens, said goggle frame including a front portion having means for mounting said lens and a rear portion having a periphery contoured to engage the face of a wearer, said goggle frame including a top portion for positioning approximately above the eyes of the wearer and a bottom portion for positioning approximately below the eyes of the wearer;
    said goggle frame having a frame opening therein to allow the transfer of air into or out of the goggle frame;
    shield means mounted onto said goggle frame over said frame opening for providing a shield opening in fluid communication with but spaced from said frame opening; and
    said goggle frame including fluid drain means recessed in said goggle frame surface and positioned between said goggle frame opening and said shield opening and extending outwardly of said shield means for preventing fluid flow through said goggle frame opening and for transferring fluid entering said shield opening away from said goggle frame opening and outwardly of said shield means to thereby substantially prevent the undesirable entry of chemical splash or other foreign materials through the goggle frame opening into contact with the eyes of the wearer.

2. The structure set forth in claim 1, including:
    said goggle frame opening being recessed for rearward exposure.

3. The structure set forth in claim 1, wherein said fluid drain means includes:
    a recessed channel formed in said goggle frame below said shield means for receiving fluid entering said shield opening.

4. The structure set forth in claim 3, including:
    said recessed channel extending in said frame body outwardly of said shield means for transferring fluid flowing into said shield opening back to the outside of said goggle frame.

5. The structure set forth in claim 3, including:
    a ridge positioned in said recessed channel between said shield means opening and said goggle frame opening to direct liquids away from said frame opening.

6. The structure set forth in claim 1, including:
    said frame opening being located in the top portion of said goggle frame end being oblong in shape; and
    said shield means including a shield cap mounted onto said frame over said frame opening and extending rearwardly to cooperate with said frame to form a rearwardly facing shield opening.

7. The structure set forth in claim 6, wherein said fluid drain means includes:
    a recessed groove formed in said frame adjacent to said frame opening and between said frame opening and said shield opening, said groove being oblong in shape but extending outwardly from under said shield cap; and
    a flow barrier ridge formed in said groove for directing outwardly of said groove undesirable liquids.

8. The structure set forth in claim 1, including:
    said bottom portion of said frame including a bottom opening, said frame including a curved entry section formed integrally with said frame and extending inwardly of said frame over said bottom opening to prevent direct entry of deleterious fluid into the interior of said frame.

* * * * *